(12) United States Patent
Haller et al.

(10) Patent No.: US 8,352,046 B1
(45) Date of Patent: Jan. 8, 2013

(54) SOUND PROCESSING ASSEMBLY FOR USE IN A COCHLEAR IMPLANT SYSTEM

(75) Inventors: Matthew I Haller, Valley Village, CA (US); Patrick T. Wong, Torrance, CA (US); Tracey Kruger, Valencia, CA (US); Lee F Hartley, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 359 days.

(21) Appl. No.: 12/697,028

(22) Filed: Jan. 29, 2010

Related U.S. Application Data

(60) Provisional application No. 61/148,648, filed on Jan. 30, 2009.

(51) Int. Cl.
*A61N 1/18* (2006.01)
(52) U.S. Cl. .......................................... 607/137
(58) Field of Classification Search .............. 607/55–57, 607/136, 137
See application file for complete search history.

(56) References Cited

U.S. PATENT DOCUMENTS

| | | | |
|---|---|---|---|
| 6,307,526 B1* | 10/2001 | Mann | 345/8 |
| 7,174,214 B2* | 2/2007 | Seligman | 607/57 |
| 7,512,448 B2* | 3/2009 | Malick et al. | 607/136 |
| 7,869,883 B2* | 1/2011 | Seligman | 607/57 |
| 7,899,543 B2* | 3/2011 | Hartley et al. | 607/57 |
| 2004/0073275 A1* | 4/2004 | Maltan et al. | 607/57 |
| 2006/0122664 A1* | 6/2006 | Sacha et al. | 607/57 |
| 2006/0178553 A1* | 8/2006 | Neisz et al. | 600/25 |
| 2007/0016267 A1* | 1/2007 | Griffin et al. | 607/57 |
| 2009/0067653 A1* | 3/2009 | Meskens et al. | 381/315 |

* cited by examiner

*Primary Examiner* — Brian T Gedeon
(74) *Attorney, Agent, or Firm* — Henricks, Slavin & Holmes LLP

(57) ABSTRACT

An exemplary cochlear implant system includes a sound processing assembly configured to be external to a patient and first and second extension members coupled to the sound processing assembly. The sound processing assembly includes a sound processing unit configured to process an audio signal and transmit one or more control parameters based on the audio signal to an implantable cochlear stimulator and a battery module configured to be electrically coupled to the sound processing unit and provide operating power to the sound processing unit. The first extension member has a distal portion configured to be coupled to a first ear of the patient and the second extension member has a distal portion configured to be coupled to a second ear of the patient. The first and second extension members typically extend back from the ears, thus positioning the sound processing assembly behind the patient's head.

19 Claims, 8 Drawing Sheets

SOUND PROCESSING ASSEMBLY FOR USE IN A COCHLEAR IMPLANT SYSTEM

This application claims the benefit of U.S. Provisional Patent Application Ser. No. 61/148,648, filed Jan. 30, 2009, which application is incorporated herein by reference in its entirety.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that audio signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce audio signals into auditory nerve impulses. People who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an array of electrodes may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to auditory nerves within the cochlea via one or more of the electrodes.

Traditional cochlear implant systems include a behind-the-ear ("BTE") sound processing unit configured to communicate with an implantable cochlear stimulator. The BTE sound processing unit includes both a processor and removable battery module, and may also include a removable microphone. Hence, the BTE unit can seem quite heavy to the patient after being worn all day. Many cochlear implant patients would like to be able to reduce the size and weight of what is worn on the ear, but do not want to sacrifice battery capacity by using a smaller battery module.

SUMMARY

In accordance with the invention(s) described and claimed herein, exemplary cochlear implant systems include a sound processing assembly configured to be external to a patient and first and second extension members coupled to the sound processing assembly. The sound processing assembly includes a sound processing unit configured to process an audio signal and transmit one or more control parameters based on the audio signal to an implantable cochlear stimulator (also referred to as a "cochlear implant", or "CI"). The sound processing assembly also includes a battery module configured to be electrically coupled to the sound processing unit and provide operating power to the sound processing unit and the CI. The first extension member has a distal portion configured to be coupled to a first ear of the patient and the second extension member has a distal portion configured to be coupled to a second ear of the patient.

Additional or alternative cochlear implant systems include a bilateral sound processing assembly configured to be external to a patient and first and second extension members coupled to the bilateral sound processing assembly. The bilateral sound processing assembly includes a sound processing unit configured to process an audio signal and transmit one or more control parameters based on the audio signal to a first cochlear implant, or CI-1, corresponding to a first ear of the patient and to a second cochlear implant, or CI-2, corresponding to a second ear of the patient, and a battery module configured to be electrically coupled to the sound processing unit and provide operating power to the sound processing unit. The first extension member has a distal portion configured to be coupled to the first ear and the second extension member has a distal portion configured to be coupled to the second ear.

Additional or alternative cochlear implant systems include: (1) a first cochlear implant, or CI-1, configured to apply electrical stimulation representative of an audio signal to a stimulation site within a right cochlea of a patient in accordance with one or more control parameters; (2) a second cochlear implant, or CI-2, configured to apply electrical stimulation representative of the audio signal to a stimulation site within a left cochlea of the patient in accordance with one or more other control parameters; and (3) a bilateral sound processing assembly configured to be external to the patient. The bilateral sound processing assembly includes a sound processing unit configured to process the audio signal and transmit the control parameters to the CI-1 and/or the CI-2, as required. A battery module provides operating power to the sound processing unit, as well as to the CI-1 and the CI-2. The battery module may be detachably coupled to the sound processing unit.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Exemplary cochlear implant systems and methods are described herein. In some examples, the systems include a sound processing assembly configured to be external to a patient along with first and second extension members coupled to the sound processing assembly. The sound processing assembly includes a sound processing unit configured to process an audio signal and transmit one or more control parameters based on the audio signal to an implantable cochlear stimulator, or cochlear implant ("CI"), and a battery module configured to be electrically coupled to the sound processing unit and provide operating power to the sound processing unit. The battery module also will typically provide operating power to the CI. The first extension member has a distal portion configured to be coupled to a first ear of the patient and the second extension member has a distal portion configured to be coupled to a second ear of the patient. In at least some implementations, the first and second extension members may be rigid.

The systems and methods described herein are advantageous in many instances because they reduce the size and weight of what a cochlear implant patient has to wear behind his or her ears. They also facilitate removable coupling of the battery module to the sound processing unit, which allows a patient to interchange the type of battery module that is used to provide power to the sound processing unit. Additional or alternative advantages of the present systems and methods are described in more detail below.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

To facilitate an understanding of the methods and systems described herein, an exemplary cochlear implant system 100 will now be described in connection with FIG. 1. Exemplary cochlear implant systems suitable for use as described herein include, but are not limited to, those disclosed in U.S. Pat. Nos. 4,400,590; 4,532,930; 4,592,359; 4,947,844; 5,824,022; 6,219,580; 6,272,382; and 6,308,101. All of these listed patents are incorporated herein by reference in their respective entireties.

Figure 1:
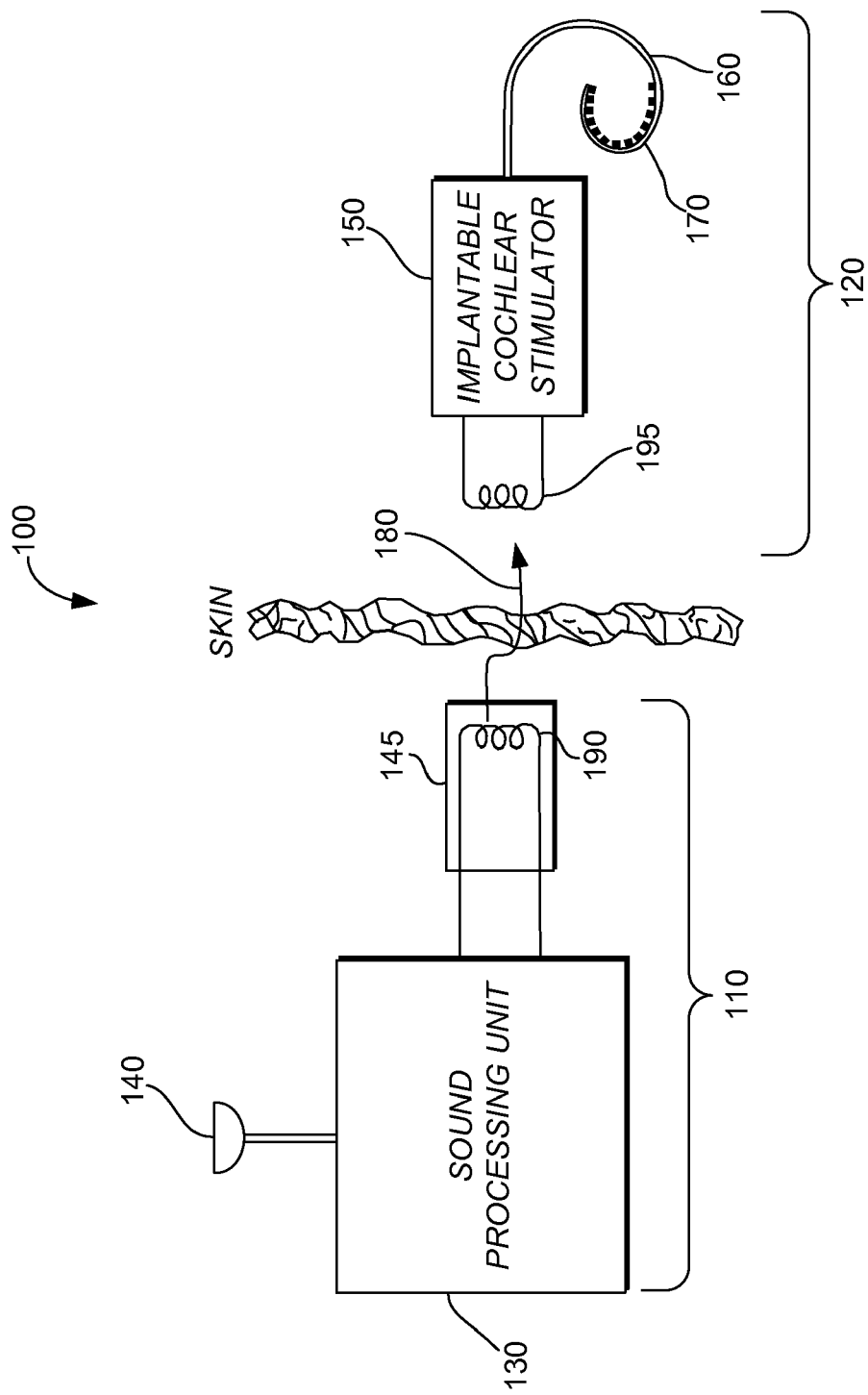
FIG. 1 illustrates an exemplary cochlear implant (CI) system according to principles described herein.

As shown in FIG. 1, the cochlear implant system 100, also referred to herein as a cochlear prosthesis, includes an external sound processor portion 110 and an implanted cochlear stimulation portion 120. The sound processor portion 110 may include a sound processing unit 130, a microphone 140, a headpiece 145, and/or additional circuitry as best serves a particular application. The cochlear stimulation portion 120 (also referred to sometimes as a cochlear implant, or "CI", portion) may include an implantable cochlear stimulator (ICS) 150, a lead 160 with an array of electrodes 170 disposed thereon, and/or additional circuitry as best serves a particular application. It will be recognized that the sound processor portion 110 may alternatively be located internal to the patient.

The microphone 140 of FIG. 1 is configured to sense audio signals and convert the sensed signals to corresponding electrical signals. In some examples, the audio signal may include speech. The audio signal may additionally include music, noise, and/or other sounds. The electrical signals are sent to the sound processing unit 130 over an electrical or other suitable link. Alternatively, the microphone 140 may be connected directly to, or integrated with, the sound processing unit 130.

The sound processing unit 130 may include any combination of hardware, software, and/or firmware as best serves a particular application. For example, the sound processing unit 130 may include one or more processors, digital signal processors (DSPs), filters, programmable memory units, storage mediums, etc.

In some examples, the sound processing unit 130 may be configured to process the converted audio signals in accordance with a selected sound processing strategy to generate appropriate stimulation parameters for controlling the electrical stimulation generated by the implantable cochlear stimulator 150. The stimulation parameters may control various parameters of the stimulation current applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

The lead 160 of FIG. 1 is adapted to be inserted within a duct of a patient's cochlea. As shown in FIG. 1, the lead 160 includes an array of electrodes 170 disposed along its length. It will be recognized that any number of electrodes 170 may be disposed along the lead 160 as may serve a particular application.

Each of the electrodes 170 is electrically coupled to the implantable cochlear stimulator 150. Electronic circuitry within the implantable cochlear stimulator 150 may therefore be configured to apply stimulation current to selected pairs or groups of electrodes 170 in accordance with a specified stimulation pattern controlled by the sound processing unit 130.

As mentioned, the implantable cochlear stimulator 150 and lead 160 may be implanted within the patient while the sound processing unit 130 and the microphone 140 are configured to be located outside the patient, e.g., behind the ear. Hence, the implantable cochlear stimulator 150 and the sound processing unit 130 may be transcutaneously coupled via a suitable data or communications link 180. The communications link 180 allows power and control signals to be sent from the sound processing unit 130 to the implantable cochlear stimulator 150. In some embodiments, data and status signals may also be sent from the implantable cochlear stimulator 150 to the sound processing unit 130.

The external and implantable portions of the cochlear implant system 100 may each include one or more coils configured to transmit and receive power and/or control signals via the data link 180. For example, the external portion 110 of the cochlear implant system 100 may include an external coil 190 disposed within headpiece 145, which may be configured to be affixed to the patient's head. The implantable portion of the cochlear implant system 120 may include an implantable coil 195 configured to be inductively coupled to the external coil 190, thereby allowing data and power signals to be wirelessly transmitted between the external portion and the implantable portion of the cochlear implant system 100. Because in certain embodiments, the external portion 110 of the cochlear implant system 100 may not always be within close proximity to the implantable portion of the cochlear implant system 120, such as when the external portion 110 is removed for sleeping, the system may be configured to recognize when the implantable coil 195 and the external coil 190 are within range of one another.

The sound processing unit 130 and the implantable cochlear stimulator 150 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels, channel acoustic gain parameters, front and backend dynamic range parameters, current steering leakage parameters, pulse rate values, pulse width values, filter characteristics, and dynamic compression parameters. Many other control parameters may be specified as may serve a particular application.

In some examples, a patient may be fitted with two cochlear implant systems 100—one for each ear. In such a bilateral configuration, a first implantable cochlear stimulator 150 is implanted within a first ear and a second implantable cochlear stimulator 150 is implanted within a second ear. First and second sound processing units 130 may be configured to control an operation of the first and second implantable cochlear stimulators 150, respectively.

Figure 2:
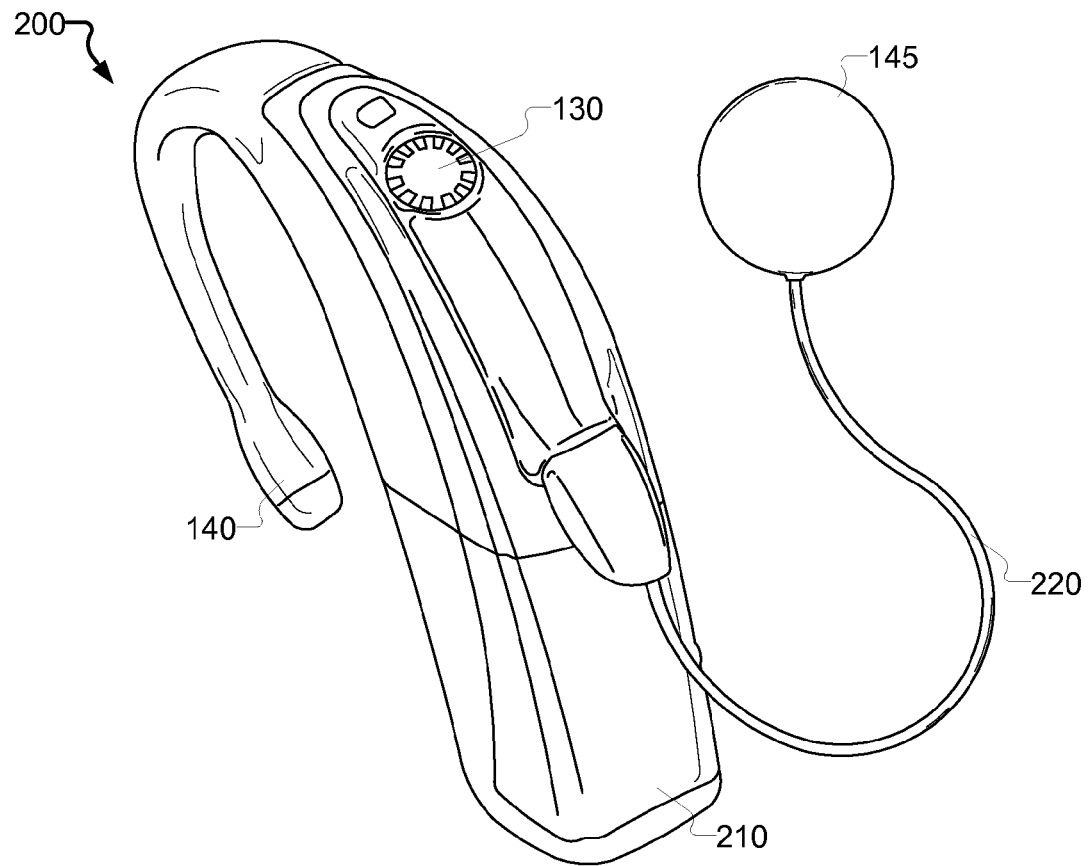
FIG. 2 illustrates an exemplary behind the ear (BTE) unit according to principles described herein.

In some examples, the sound processing unit 130 may be embodied by or included within a BTE unit. FIG. 2 illustrates an exemplary BTE unit 200. As shown in FIG. 2, the BTE unit 200 may include sound processing unit 130, a battery module 210, and microphone 140 coupled one to another. In some examples, the BTE unit 200 may be removably coupled to headpiece 145 via a cable 220.

Battery module 210 may be configured to provide operating power for one or more components of the BTE unit 200. In some examples, the battery module 210 may be selectively removed from the sound processing unit 130. In this manner, differently sized battery units 210 may be coupled to the sound processing unit 130 in order to provide a desired amount of operating power to the components of the BTE unit 200. In general, as the size of the battery module 210 increases, the longer the BTE unit 200 may operate before having to recharge or replace the battery module 210.

As shown in FIG. 2, the BTE unit 200 may be dimensioned such that it may be worn behind the ear. However, as mentioned, the BTE unit 200 may seem quite heavy to a patient after being worn all day, especially when a relatively large battery module 210 is attached to the sound processing unit 130. Moreover, the positioning of the BTE unit 200 behind the ear may impede the ability of the patient to participate in sports, exercise, and/or other physical activities that may cause the BTE unit 200 to become dislodged or otherwise damaged. In addition, BTE units 200 are readily noticeable and are often a source of embarrassment to cochlear implant patients, especially children. These drawbacks of BTE units 200 are exasperated for bilateral cochlear implant patients.

To this end, the systems and methods described herein provide configurations wherein one or more components of a cochlear implant system 100 may be worn behind the head or at some other convenient location. These configurations, as will be described in more detail below, minimize many of the inconveniences and drawbacks of traditional cochlear implant systems.

Figure 3:
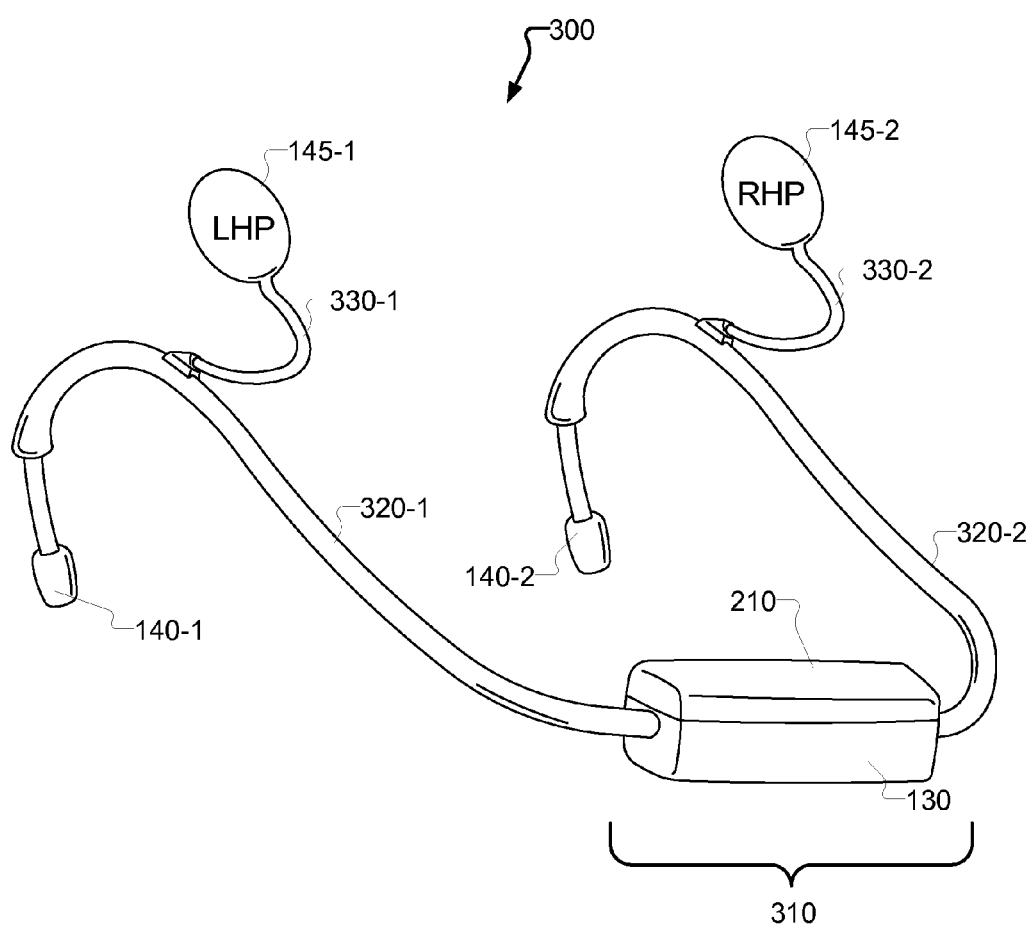
FIG. 3 illustrates an exemplary external sound processor portion that may be a part of a cochlear implant system according to principles described herein.

FIG. 3 illustrates an exemplary external sound processor portion 300 that may be a part of a cochlear implant system 100. As shown in FIG. 3, a sound processing assembly 310 may be coupled to first and second extension members 320-1 and 320-2, collectively referred to herein as "extension members 320". The sound processing assembly 310 may include a battery module 210 removably coupled to a sound processing unit 130 which has a length that is substantially greater than its height and width. To this end, the battery module 210 may include a connector assembly (not shown) configured to be removably coupled to a corresponding connector assembly (not shown) that is a part of the sound processing unit 130.

Because the battery module 210 is removably coupled to the sound processing unit 130, the battery module 210 may be easily interchanged with other battery modules 210 as may serve a particular application.

The external sound processor portion 300 shown in FIG. 3 may be configured to be used by a bilateral cochlear implant patient. To this end, the sound processing unit 130 may include a bilateral sound processing unit 130 that is configured to control the operation of implantable cochlear stimulators 150 (see FIG. 1), there being one cochlear stimulator implanted in each ear of a patient, or a total of two cochlear stimulators 150. In some examples, a single sound processing unit 130 configured to control both implantable cochlear stimulators 150 eliminates redundant circuits and/or components that may be present in separate sound processing units 130. However, in some alternative examples, as will be described in more detail below, the sound processing assembly 300 may include first and second sound processing units 130 each configured to control a corresponding implantable cochlear stimulator 150.

As shown in FIG. 3, the sound processing assembly 310 may be generally elongate (i.e., long and thin) so as to be able to fit behind a head of the patient. In some examples, the sound processing assembly 310 may be contoured or otherwise fitted to the head of a particular patient to optimize fitting, comfort, and/or aesthetic appeal. In some examples, the sound processing assembly 310 may be at least partially surrounded by a housing or encasing made out of any suitable material.

Extension members 320 may be coupled at a proximal end to the longitudinal ends of the sound processing assembly 310 and configured to extend in a generally perpendicular direction from the sound processing assembly 310, similar to eyeglasses arm members. As shown in FIG. 3, the distal portions of the extension members 320 may be generally curved so that they may be worn behind the ears of a patient. It will be recognized that the distal portion of the extension members 320 may alternatively have any other shape as may serve a particular application. For example, the distal portion of the extension members 320 may be generally straight or of any other suitable shape or dimension. In some examples, one or more of the extension members 320 may be configured to house one or more conductive wires or other components of the external sound processor portion 300.

In some examples, a microphone 140 may be coupled to a distal end of each extension member 320 such that the microphone 140 is positioned adjacent to or near the opening of the ear. For example, microphone 140-1 is coupled to the distal end of extension member 320-1 and microphone 140-2 is coupled to the distal end of extension member 320-2. The microphones 140 may alternatively be coupled to any other component of the external sound processor portion 300 as may serve a particular application.

The sound processing unit 130 may be electrically coupled to one or more headpieces (e.g., headpieces 145-1 and 145-2, collectively referred to herein as "headpieces 145") via one or more corresponding cables (e.g., cables 330-1 and 330-2, collectively referred to herein as "cables 330"). The cables 330 may be made out of any suitable material. In some examples, the cables 330 may be physically coupled to the extension members 320, as shown in FIG. 3. In this example, one or more conductive wires configured to facilitate electrical coupling of the headpieces 145 to the sound processing unit 130 may be disposed within cable 330 and/or within the extension members 330. In some alternative examples, the cables 330 may be coupled directly to the sound processing unit 130, as described below in connection with FIG. 4. In yet other alternative examples, the headpieces 145 may be wirelessly coupled to the sound processing unit 130.

Figure 4:
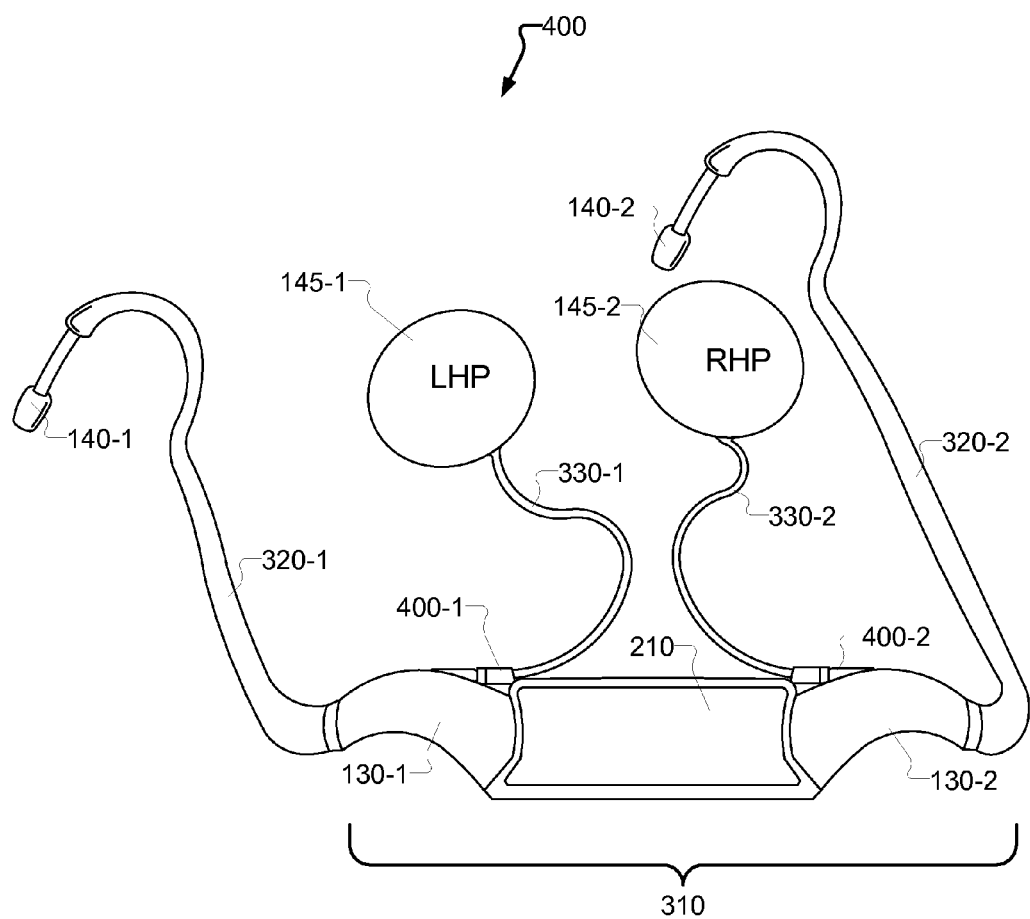
FIG. 4 illustrates another exemplary external sound processor portion that may be a part of a bilateral cochlear implant system according to principles described herein.

FIG. 4 illustrates another exemplary external sound processor portion 400 that may be a part of a bilateral cochlear implant system 100. As shown in FIG. 4, the sound processing assembly 310 may include first and second sound processing units 130-1 and 130-2, referred to herein as "sound processing units 130". Each sound processing unit 130 is configured to control a corresponding implantable cochlear stimulator 150. For example, sound processing unit 130-1 may be configured to control an implantable cochlear stimulator 150 having its lead 160, and associated electrodes 170 (see FIG. 1), placed within the cochlea of the left ear. Similarly, sound processing unit 130-2 may be configured to control an implantable cochlear stimulator 150 having its lead 160, and associated electrodes 170, placed within the cochlear the right ear.

In some examples, the battery module 210 may be removably coupled to one or both of the sound processing units 130. To this end, the battery module 210 may include connector assemblies disposed at both ends thereof, wherein each of the connector assemblies are configured to be coupled to corresponding connector assemblies that are part of the sound processing units 130.

As shown in FIG. 4, the cables 330-1 and 330-2, configured to couple the headpieces 145 to their respective sound processing units 130, may be coupled directly to the sound processing units 130. To this end, the sound processing units 130 may each include a connector assembly (e.g., connector assembly 400-1 and connector assembly 400-2) configured to facilitate coupling of the cables 330 to their respective sound processing units 130.

Figure 5:
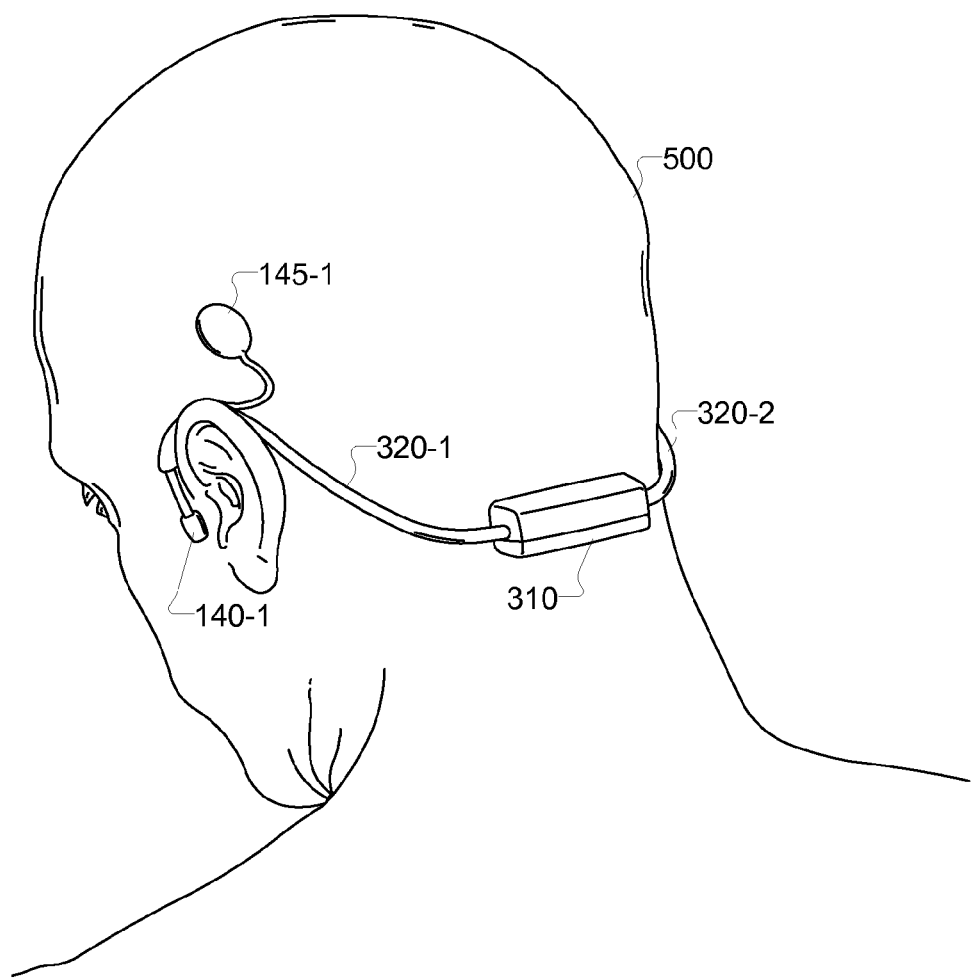
FIG. 5 shows an exemplary configuration wherein a sound processing assembly is worn behind the head of a patient according to principles described herein.

As mentioned, the sound processing assembly 310 may be configured to be worn behind the head of a patient. To illustrate, FIG. 5 shows an exemplary configuration wherein the sound processing assembly 310 is worn behind the head 500 of a patient. As shown in FIG. 5, the extension members 320 are worn behind the ears such that the elongate sound processing assembly 310 is positioned horizontally behind the head 500. By positioning the sound processing assembly 310 behind the head 500, the size and weight of what is worn behind the ears is reduced.

Figure 6:
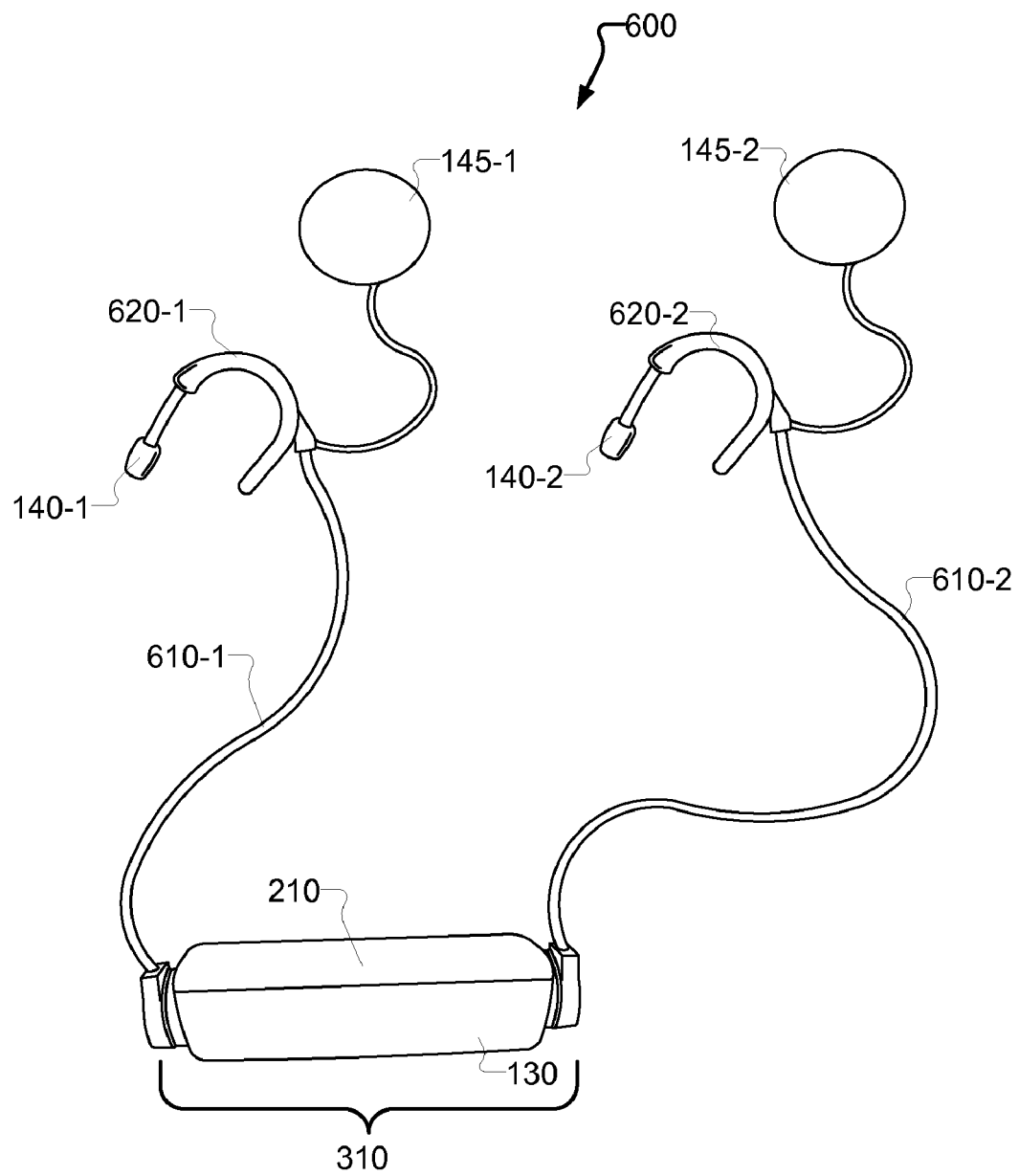
FIG. 6 illustrates another exemplary external sound processor portion that may be a part of a bilateral cochlear implant system according to principles described herein.

The sound processing assembly 310 may be alternatively worn by a patient at any other suitable location. For example, FIG. 6 illustrates another exemplary external sound processor portion 600 that may be a part of a bilateral cochlear implant system 100 wherein the sound processing assembly 310 is configured to be worn by a patient at any suitable location. As shown in FIG. 6, cables 610-1 and 610-2, collectively referred to herein as "cables 610", may be coupled to the sound processing assembly 310. Each cable is coupled to an earpiece (e.g., earpiece 620-1 and earpiece 620-2, collectively referred to herein as "earpieces 620"). The earpieces 620 are configured to be worn behind the ears of the patient. Each earpiece 620 is coupled to a corresponding microphone 140 and to a corresponding headpiece 145. It will be recognized that the microphones 140 and headpieces 145 may alternatively be coupled to the sound processing assembly 310 in any other way as may serve a particular application.

The cables 610 may be of any suitable length and may be flexible so as to allow the sound processing assembly 310 to be worn by the patient at any suitable location. To this end, the sound processing assembly 310 may include a clip assembly or other affixation assembly configured to allow the patient to clip or otherwise attach the sound processing assembly 310 to a belt, piece of clothing, or other object.

Figure 7:
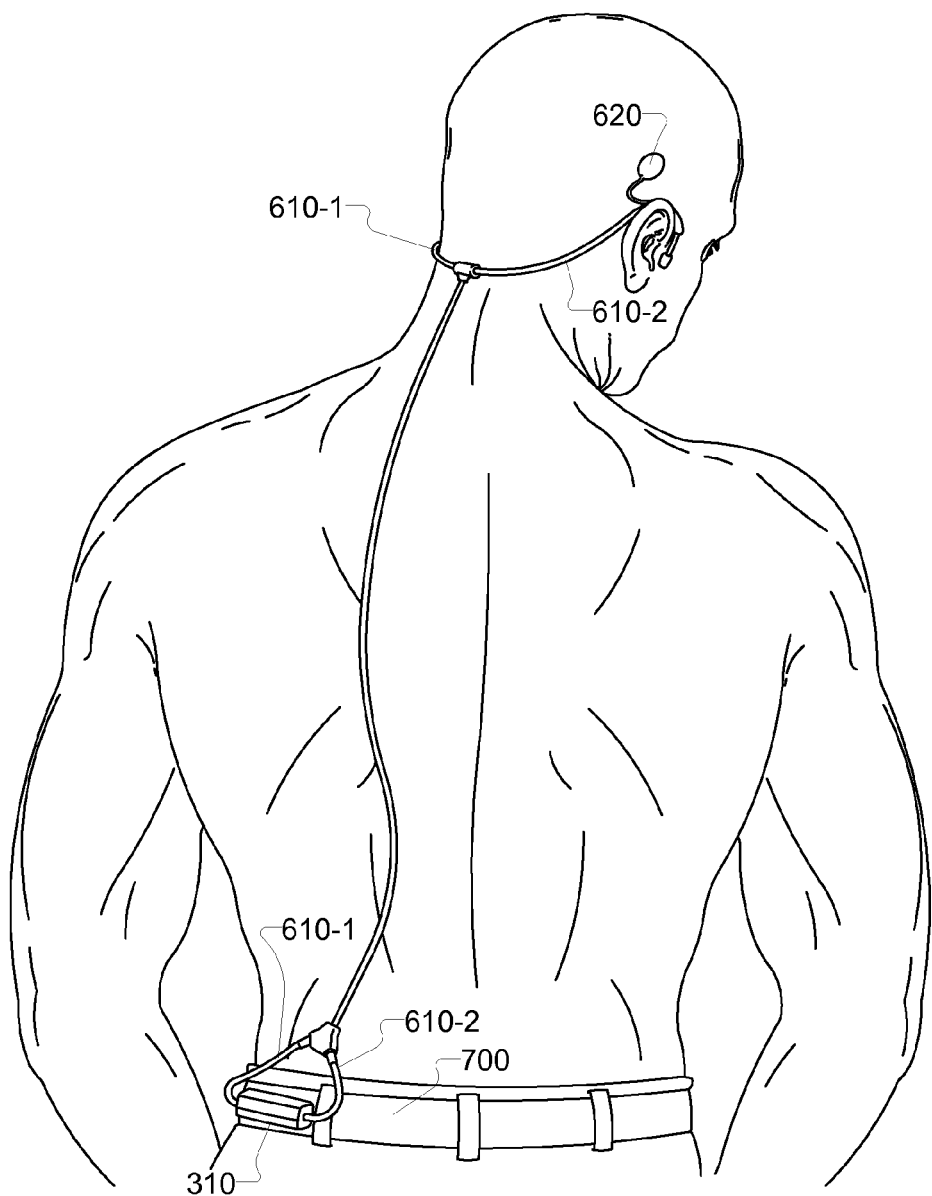
FIG. 7 shows an exemplary configuration wherein a sound processing assembly is attached to a belt of a patient according to principles described herein.

To illustrate, FIG. 7 shows an exemplary configuration wherein the sound processing assembly 310 is attached to a belt 700 of a patient. The sound processing assembly 310 may be attached to the belt 700 in any suitable manner. For example, the sound processing assembly 310 may include a clip assembly configured to clip to the belt. It will be recognized that the sound processing assembly 310 may be attached to any other piece of clothing or to any body part as may serve a particular application.

As shown in FIG. 7, the cables 610 are joined together near the sound processing assembly 310 and are then routed to the ears of the patient, where they are separated again. In this manner, entanglement of the cables 610 may be minimized. As shown in FIG. 7, the cables 610 are long enough to allow the sound processing assembly 310 to be attached to belt 700 when the earpieces 620 are worn behind the ear. The configuration of FIG. 7 is advantageous in many situations wherein the patient desires to hide the sound processing assembly 310 from view and/or avoid excessive weight on the ears.

In some instances, a cochlear implant patient may desire to participate in sports, exercise, and/or other physical activities. To this end, one or more components of the external sound processor portion 300 may be placed within a protective "sleeve." The sleeve may be made out of any suitable material (e.g., neoprene, rubber, etc.). The sleeve is configured to protect one or more components of the external sound processor portion 300 from one or more environmental factors that the patient may encounter, such as rain, snow, dust, water, etc. The sleeve also may be used to prevent one or more components of the external sound processor portion 300 from becoming dislodged from the patient while the patient is engaged in sporting or other activities that may require sudden movements of the head.

Figure 8:
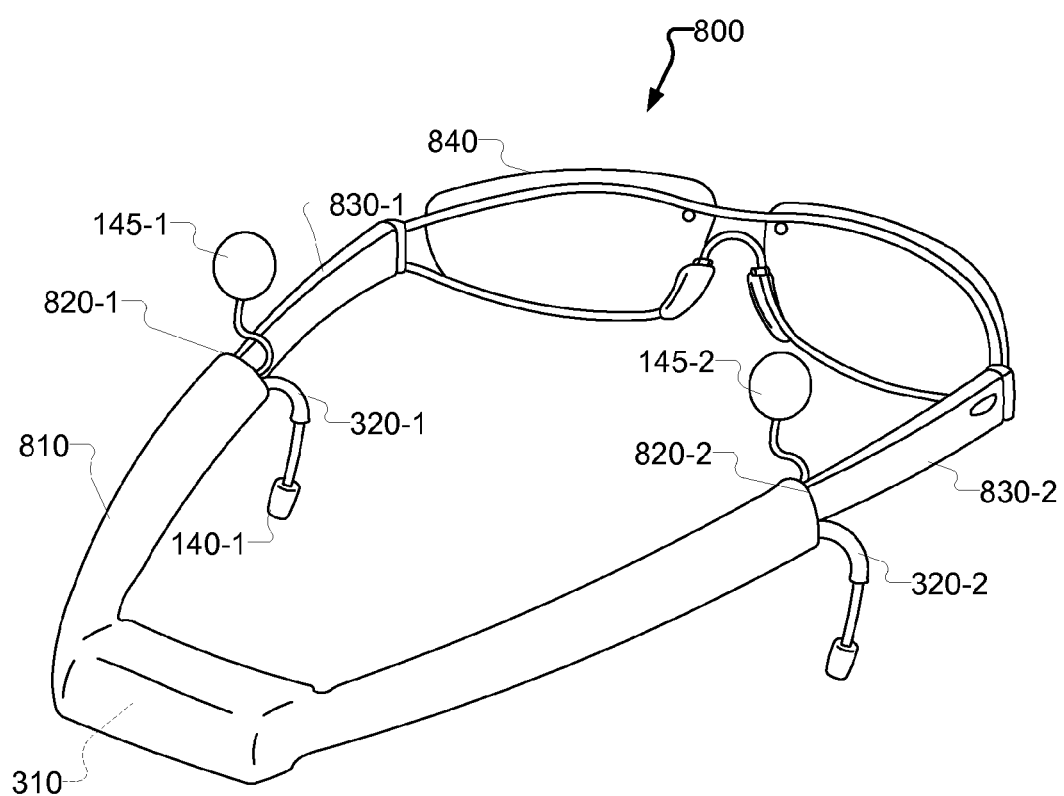
FIG. 8 illustrates an exemplary configuration wherein a sleeve at least partially surrounds the extension members and the sound processing assembly according to principles described herein.

FIG. 8 illustrates an exemplary configuration 800 wherein a sleeve 810 at least partially surrounds the extension members 320 and the sound processing assembly 310. As shown in FIG. 8, distal ends 820-1 and 820-2, collectively referred to herein as " "distal ends 820", of the sleeve 810 may be configured to fit over or otherwise couple to corresponding arm members 830-1 and 830-2 of eyeglasses 840. In this manner, a patient with eyeglasses 840 may utilize the sleeve 810 to securely fasten the sound processing assembly 310 to the eyeglasses 840.

In some examples, the sleeve 810 may include a slit extending at least partially along its length. The slit may allow the patient to remove the sound processing assembly 310 and extension members 320 from the sleeve 810.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A cochlear implant system comprising:
a sound processing assembly configured to be worn behind a head of a patient, said sound processing assembly including
a sound processing unit configured to process an audio signal and transmit one or more control parameters based on said audio signal to an implantable cochlear stimulator, said sound processing unit defining a length, first and second longitudinal ends, a height and a width, the length being greater that the height and the width, and
a battery module configured to be electrically coupled to said sound processing unit and provide operating power to said sound processing unit;
a first extension member having a distal portion configured to be coupled to a first ear of said patient and a proximal end coupled to the first longitudinal end of said sound processing unit; and
a second extension member having a distal portion configured to be coupled to a second ear of said patient and a proximal end coupled to the second longitudinal end of said sound processing unit.

2. The system of claim 1, wherein said sound processing unit comprises a bilateral sound processing unit.

3. The system of claim 1, wherein said sound processing unit comprises:
a first sound processing unit configured to process said audio signal and transmit said one or more control parameters to said implantable cochlear stimulator; and
a second sound processing unit configured to process said audio signal and transmit said one or more control parameters to another implantable cochlear stimulator.

4. The system of claim 1, wherein said battery module is configured to be removably coupled to said sound processing unit.

5. The system of claim 4, wherein said battery module includes at least one connector assembly configured to facilitate removal of said battery module from said sound processing unit.

6. The system of claim 1, further comprising at least one microphone coupled to at least one of said first and second extension members.

7. The system of claim 1, further comprising a headpiece coupled to at least one of said first and second extension members.

8. The system of claim 1, further comprising a headpiece coupled to said sound processing unit.

9. A cochlear implant system comprising:
a sound processing assembly configured to be external to a patient, said sound processing assembly including
a sound processing unit configured to process an audio signal and transmit one or more control parameters based on said audio signal to an implantable cochlear stimulator, said sound processing unit defining a length, first and second longitudinal ends, a height and a width, the length being greater that the height and the width, and
a battery module configured to be electrically coupled to said sound processing unit and provide operating power to said sound processing unit;
a first extension member having a distal portion configured to be coupled to a first ear of said patient and a proximal end coupled to the first longitudinal end of said sound processing unit;
a second extension member having a distal portion configured to be coupled to a second ear of said patient and a proximal end coupled to the second longitudinal end of said sound processing unit; and
a sleeve configured to at least partially surround said sound processing assembly and said first and second extension members.

10. The system of claim 9, wherein said sleeve is configured to removably couple to first and second arm members of eyeglasses.

11. The system of claim 9, wherein said sleeve is made out of neoprene.

12. The system of claim 9, wherein said sleeve includes a slit extending at least partially along a length of said sleeve.

13. A head-mounted system for use with first and second implantable cochlear stimulators, the system comprising:
a bilateral sound processing assembly configured to be external to the head of a patient, said bilateral sound processing assembly including
a sound processing unit configured to process an audio signal and transmit one or more control parameters based on said audio signal to a first implantable cochlear stimulator corresponding to a first ear of said patient and to a second implantable cochlear stimulator corresponding to a second ear of said patient, and
a battery module configured to be electrically coupled to said sound processing unit and provide operating power to said sound processing unit; and
first and second extension members coupled to said bilateral sound processing assembly, said first extension member having a distal portion configured to be coupled to said first ear of said patient and said second extension member having a distal portion configured to be coupled to said second ear of said patient;
wherein the respective configurations of said bilateral sound processing assembly and the first and second extension members are such that said bilateral sound processing assembly will be positioned behind said patient's head when said first and second extension members are coupled to the first and second ears of said patent.

14. The system of claim 13, wherein said sound processing unit comprises:
a first sound processing unit configured to process said audio signal and transmit said one or more control parameters to said first implantable cochlear stimulator; and
a second sound processing unit configured to process said audio signal and transmit said one or more control parameters to said second implantable cochlear stimulator.

15. The system of claim 13, wherein said battery module is configured to be removably coupled to said sound processing unit.

16. The system of claim 15, wherein said battery module includes at least one connector assembly configured to facilitate detachable connection of said battery module to said sound processing unit.

17. A bilateral cochlear implant system comprising:
a first implantable cochlear stimulator configured to apply electrical stimulation representative of an audio signal to a stimulation site within a right cochlea of a patient in accordance with one or more control parameters;
a second implantable cochlear stimulator configured to apply electrical stimulation representative of said audio signal to a stimulation site within a left cochlea of said patient in accordance with one or more other control parameters;

a bilateral sound processing assembly configured to be external to said patient, said bilateral sound processing assembly including
 a sound processing unit configured to process said audio signal and transmit said control parameters to said first and second implantable cochlear stimulators, and
 a battery module configured to provide operating power to said sound processing unit and configured to be removably coupled to said sound processing unit; and
first and second rigid extension members coupled to said bilateral sound processing assembly, said first rigid extension member having a distal portion configured to be coupled to a first ear of said patient and a second rigid extension member having a distal portion configured to be coupled to a second ear of said patient, wherein the patient can wear the sound processing unit behind his or her head with the first and second rigid extension members extending over the patient's first and second ears, respectively.

18. The system of claim 17, further comprising first and second cables coupled to said bilateral sound processing assembly, said first cable having a distal portion coupled to a first earpiece configured to be worn on or in said first ear, and said second cable having a distal portion coupled to a second earpiece configured to be worn on or in said second ear.

19. The system of claim 17, wherein
 said first extension member includes a proximal portion adjacent to said bilateral sound portion, and said first extension member is rigid from the proximal portion to the distal portion; and
 said second extension member includes a proximal portion adjacent to said bilateral sound portion, and said second extension member is rigid from the proximal portion to the distal portion.

* * * * *